(12) United States Patent  
Schiehser et al.

(10) Patent No.: US 9,783,497 B1  
(45) Date of Patent: Oct. 10, 2017

(54) DETERMINING DEGRADATION OF 3,4-DIAMINOPYRIDINE

(71) Applicant: Jacobus Pharmaceutical Company, Inc., Princeton, NJ (US)

(72) Inventors: Guy Alan Schiehser, Washington Crossing, PA (US); Rajendra Shah, Edison, NJ (US); Wenyi Zhao, Monroe Township, NJ (US)

(73) Assignee: Jacobus Pharmaceuticals, Inc., Princeton, NJ (US)

( * ) Notice: Subject to any disclaimer, the term of this patent is extended or adjusted under 35 U.S.C. 154(b) by 0 days.

(21) Appl. No.: 15/179,060

(22) Filed: Jun. 10, 2016

(51) Int. Cl.  
    *G01N 24/00* (2006.01)  
    *C07D 213/73* (2006.01)  
    *G01N 30/74* (2006.01)  
    *G01N 30/02* (2006.01)

(52) U.S. Cl.  
    CPC ........... *C07D 213/73* (2013.01); *G01N 30/74* (2013.01); *G01N 2030/027* (2013.01)

(58) Field of Classification Search  
    USPC .......................................................... 436/161  
    See application file for complete search history.

(56) References Cited

PUBLICATIONS

Do, B. et al. HPLC Method for Determination of 3,4-Diaminopyridine in the Presence of Related Substances and Degradation Products Formed Under Stress Conditions, 2006, Chromatographia, vol. 62, (No. 11/12), pp. 599-603.*  
Glusker et al., Crystal, Structure Analysis: A Primer, 2d. ed. Oxford Univ. Press, New York (1985), p. 87.  
International Tables for Crystallography, vol. C, Kluwer Academic Publishers: Dordrecht, The Netherlands, 1992, Tables 4.2.6.8 and 6.1.1.4.  
Macrae, C.F. et al., "Mercury: Visualization and Analysis of Crystal Structures", J. Appl. Cryst., 2006, 39, 453-457.  
Otwinowski, Z. et al; "Processing of X-ray diffraction data collected in oscillation mode", Methods in Enzymology, 1997, vol. 276, pp. 307-326.  
Sheldrick, G.M., "A Short History of SHELX", Acta Cryst., 2008, A64, pp. 112-122.

* cited by examiner

*Primary Examiner* — Robert Xu  
(74) *Attorney, Agent, or Firm* — Baker & Hostetler LLP

(57) ABSTRACT

The present invention relates to methods of determining the purity of a sample of 3,4-diaminopyridine comprising determining the presence, absence, or amount of a dimer of 3,4-diaminopyridine or a dimer of 3,4-diaminopyridine in the form of a salt, solvate or complex or a combination thereof. The invention also relates to methods of detecting and quantitating degradation in a sample of 3,4-diaminopyridine. Dimers of 3,4-diaminopyridine and methods of making and isolating the same are also provided.

8 Claims, 14 Drawing Sheets

| | |
|---|---|
| formula | $C_{13}H_{20}N_6O_6S$ |
| formula weight | 364.39 |
| space group | Pbca (No. 61) |
| a, Å | 10.4259(4) |
| b, Å | 16.7836(9) |
| c, Å | 19.2638(7) |
| V, Å$^3$ | 3370.9(3) |
| Z | 8 |
| $d_{calc}$, g cm$^{-3}$ | 1.436 |
| crystal dimensions, mm | 0.25 x 0.15 x 0.08 |
| temperature, K | 295 |
| radiation (wavelength, Å) | Cu K$\alpha$ (1.54178) |
| monochromator | confocal optics |
| linear abs coef, mm$^{-1}$ | 2.097 |
| absorption correction applied | empirical$^a$ |
| transmission factors: min, max | 0.057, 0.846 |
| diffractometer | Rigaku RAPID-II |
| h, k, l range | -12 to 12  -20 to 20  -21 to 21 |
| 2θ range, deg | 4.59-144.57 |
| mosaicity, deg | 0.31 |
| programs used | SHELXTL |
| $F_{000}$ | 1536.0 |
| data collected | 13873 |
| unique data | 2838 |
| $R_{int}$ | 0.043 |
| data used in refinement | 2838 |
| cutoff used in R-factor calculations | $F_o^2 > 2.0\sigma(F_o^2)$ |
| data with I>2.0σ(I) | 2355 |
| refined extinction coef | 0.0020 |
| number of variables | 264 |
| largest shift/esd in final cycle | 0.00 |
| $R(F_o)$ | 0.0565 |
| $R_w(F_o^2)$ | 0.1596 |
| goodness of fit | 1.053 |

$^a$ Otwinowski, Z.; Minor, W. Methods Enzymol. 1997, 276, 307.

FIG. 3

Packing diagram of 3,4-diaminopyridine dimer sulfate monohydrate monomethanolate view along the crystallographic *a* axis.

Packing diagram of 3,4-diaminopyridine dimer sulfate monohydrate monomethanolate viewed along the crystallographic *b* axis.

Packing diagram of 3,4-diaminopyridine dimer sulfate monohydrate monomethanolate viewed along the crystallographic c axis.

| Atom | x | y | z | U(Å²) |
|---|---|---|---|---|
| S(1) | 0.07445(6) | 0.34690(4) | 0.05398(4) | 0.0422(2) |
| O(1) | -0.0209(2) | 0.32110(14) | 0.00191(12) | 0.0631(7) |
| O(2) | 0.1693(2) | 0.39681(17) | 0.01711(12) | 0.0724(8) |
| O(3) | 0.1380(3) | 0.27913(18) | 0.08209(16) | 0.0998(12) |
| O(4) | 0.0122(3) | 0.39586(17) | 0.10536(15) | 0.0843(9) |
| O(1W) | 0.3811(3) | 0.05878(19) | 0.08027(15) | 0.0769(9) |
| O(31) | 0.4994(3) | 0.38206(19) | 0.25240(15) | 0.0866(10) |
| N(11) | 0.3461(2) | 0.02104(13) | 0.37831(12) | 0.0438(6) |
| N(13) | 0.2985(3) | -0.17305(17) | 0.45989(18) | 0.0604(8) |
| N(14) | 0.5629(3) | -0.15431(19) | 0.46769(18) | 0.0576(9) |
| N(21) | 0.1916(3) | 0.12410(16) | 0.37679(16) | 0.0518(8) |
| N(23) | 0.3737(3) | 0.04038(18) | 0.23296(17) | 0.0616(9) |
| N(24) | 0.2346(3) | 0.16142(18) | 0.16798(15) | 0.0604(9) |
| C(12) | 0.2871(2) | -0.04525(16) | 0.40460(14) | 0.0427(7) |
| C(13) | 0.3553(2) | -0.10458(16) | 0.43628(14) | 0.0418(7) |
| C(14) | 0.4919(3) | -0.09693(17) | 0.44034(15) | 0.0437(8) |
| C(15) | 0.5472(3) | -0.02609(18) | 0.41580(16) | 0.0496(8) |
| C(16) | 0.4748(3) | 0.03071(18) | 0.38506(15) | 0.0479(8) |
| C(22) | 0.2743(3) | 0.07855(16) | 0.33970(15) | 0.0444(8) |
| C(23) | 0.2920(3) | 0.08705(15) | 0.26948(15) | 0.0431(8) |
| C(24) | 0.2213(3) | 0.14971(16) | 0.23615(16) | 0.0473(8) |
| C(25) | 0.1388(3) | 0.19553(18) | 0.27673(19) | 0.0560(9) |
| C(26) | 0.1246(3) | 0.18161(19) | 0.34538(18) | 0.0584(9) |
| C(31) | 0.3709(5) | 0.3625(3) | 0.2393(3) | 0.0977(17) |
| H(21) | 0.187(4) | 0.116(2) | 0.417(2) | 0.065(12)* |
| H(131) | 0.220(5) | -0.168(3) | 0.463(2) | 0.090(15)* |
| H(132) | 0.349(5) | -0.203(3) | 0.507(2) | 0.107(15)* |
| H(141) | 0.643(4) | -0.147(2) | 0.467(2) | 0.068(11)* |
| H(142) | 0.533(4) | -0.194(3) | 0.478(2) | 0.076(14)* |
| H(1W1) | 0.384(6) | 0.608(4) | 0.070(3) | 0.14(2)* |
| H(1W2) | 0.420(5) | 0.083(3) | 0.053(3) | 0.101(19)* |
| H(231) | 0.385(4) | 0.046(3) | 0.185(3) | 0.089(15)* |
| H(232) | 0.404(4) | 0.006(2) | 0.251(2) | 0.067(12)* |
| H(241) | 0.189(4) | 0.199(2) | 0.152(2) | 0.077(12)* |
| H(242) | 0.279(4) | 0.128(2) | 0.136(2) | 0.070(11)* |
| H(12) | 0.199 | -0.050 | 0.401 | 0.051 |
| H(15) | 0.635 | -0.018 | 0.421 | 0.060 |
| H(16) | 0.514 | 0.077 | 0.368 | 0.058 |
| H(25) | 0.093 | 0.237 | 0.256 | 0.067 |
| H(26) | 0.068 | 0.212 | 0.371 | 0.070 |
| H(31) | 0.510 | 0.388 | 0.294 | 0.130 |
| H(31A) | 0.341 | 0.325 | 0.274 | 0.147 |
| H(31B) | 0.364 | 0.339 | 0.194 | 0.147 |
| H(31C) | 0.319 | 0.410 | 0.241 | 0.147 |

Starred atoms were refined isotropically
$U_{eq} = (1/3)\Sigma_i\Sigma_j U_{ij}a_i^*a_j^*a_i \cdot a_j$
Hydrogen atoms are included in calculation of structure factors but not refined

FIG. 9

| Name | U(1,1) | U(2,2) | U(3,3) | U(1,2) | U(1,3) | U(2,3) |
|---|---|---|---|---|---|---|
| S(1) | 0.0379(4) | 0.0442(4) | 0.0446(5) | 0.0067(3) | 0.0064(2) | 0.0002(3) |
| O(1) | 0.0516(12) | 0.0629(13) | 0.0749(16) | -0.0088(10) | -0.0128(11) | 0.0000(12) |
| O(2) | 0.0581(13) | 0.1066(19) | 0.0526(14) | -0.0339(13) | -0.0039(11) | 0.0062(13) |
| O(3) | 0.129(3) | 0.0794(18) | 0.091(2) | 0.0486(18) | -0.0230(18) | 0.0148(16) |
| O(4) | 0.0738(17) | 0.0967(19) | 0.0799(18) | 0.0243(15) | 0.0141(14) | -0.0262(15) |
| O(1W) | 0.110(2) | 0.0587(15) | 0.0620(17) | -0.0012(15) | 0.0281(15) | 0.0010(14) |
| O(31) | 0.096(2) | 0.0896(19) | 0.0743(19) | -0.0257(16) | -0.0015(15) | 0.0002(17) |
| N(11) | 0.0420(12) | 0.0473(12) | 0.0420(14) | -0.0001(9) | -0.0008(9) | 0.0065(10) |
| N(13) | 0.0407(15) | 0.0524(15) | 0.088(2) | -0.0015(12) | 0.0048(13) | 0.0161(14) |
| N(14) | 0.0408(15) | 0.0560(17) | 0.076(2) | 0.0020(13) | -0.0063(13) | 0.0124(14) |
| N(21) | 0.0547(15) | 0.0582(15) | 0.0424(17) | 0.0084(12) | 0.0030(11) | 0.0008(12) |
| N(23) | 0.083(2) | 0.0575(16) | 0.0443(19) | 0.0257(15) | 0.0088(14) | 0.0087(14) |
| N(24) | 0.080(2) | 0.0529(16) | 0.0484(18) | 0.0158(14) | -0.0008(14) | 0.0121(13) |
| C(12) | 0.0354(13) | 0.0444(14) | 0.0483(17) | -0.0038(11) | 0.0019(11) | 0.0021(12) |
| C(13) | 0.0390(14) | 0.0432(14) | 0.0432(16) | 0.0003(11) | 0.0017(11) | 0.0011(12) |
| C(14) | 0.0465(15) | 0.0494(15) | 0.0412(16) | 0.0003(11) | -0.0015(11) | 0.0010(12) |
| C(15) | 0.0383(14) | 0.0606(17) | 0.0499(18) | -0.0054(12) | -0.0049(12) | 0.0070(15) |
| C(16) | 0.0432(14) | 0.0531(16) | 0.0475(17) | -0.0105(12) | -0.0014(12) | 0.0054(13) |
| C(22) | 0.0452(15) | 0.0418(14) | 0.0461(17) | 0.0026(11) | 0.0008(12) | 0.0029(12) |
| C(23) | 0.0483(15) | 0.0378(13) | 0.0433(17) | 0.0016(11) | 0.0011(12) | 0.0029(11) |
| C(24) | 0.0520(16) | 0.0384(13) | 0.0516(19) | -0.0002(12) | -0.0010(13) | 0.0033(12) |
| C(25) | 0.0606(18) | 0.0445(15) | 0.063(2) | 0.0107(13) | -0.0029(15) | 0.0034(14) |
| C(26) | 0.0595(19) | 0.0547(17) | 0.061(2) | 0.0133(15) | 0.0042(15) | -0.0023(15) |
| C(31) | 0.084(3) | 0.109(3) | 0.108(4) | -0.018(3) | -0.003(3) | 0.002(3) |

The form of the anisotropic temperature factor is:
$$\exp[-2\pi^2 h^2 a^{*2} U(1,1) + k^2 b^{*2} U(2,2) + l^2 c^{*2} U(3,3) + 2hka^*b^* U(1,2) + 2hla^*c^* U(1,3) + 2klb^*c^* U(2,3)]$$
where $a^*$, $b^*$, and $c^*$ are reciprocal lattice constants.

FIG. 10

| Atom 1 | Atom 2 | Distance | Atom 1 | Atom 2 | Distance |
|---|---|---|---|---|---|
| S(1) | O(3) | 1.423(3) | N(21) | C(22) | 1.356(4) |
| S(1) | O(4) | 1.441(2) | N(21) | H(21) | 0.80(4) |
| S(1) | O(1) | 1.477(2) | N(23) | C(23) | 1.354(4) |
| S(1) | O(2) | 1.478(2) | N(23) | H(231) | 0.93(5) |
| O(1W) | H(1W1) | 0.87(7) | N(23) | H(232) | 0.74(4) |
| O(1W) | H(1W2) | 0.78(5) | N(24) | C(24) | 1.335(4) |
| O(31) | C(31) | 1.402(5) | N(24) | H(241) | 0.86(4) |
| N(11) | C(16) | 1.358(4) | N(24) | H(242) | 0.95(4) |
| N(11) | C(12) | 1.368(3) | C(12) | C(13) | 1.367(4) |
| N(11) | C(22) | 1.430(3) | C(13) | C(14) | 1.432(4) |
| N(13) | C(13) | 1.370(4) | C(14) | C(15) | 1.403(4) |
| N(13) | H(131) | 0.82(5) | C(15) | C(16) | 1.352(4) |
| N(13) | H(132) | 1.16(5) | C(22) | C(23) | 1.373(4) |
| N(14) | C(14) | 1.325(4) | C(23) | C(24) | 1.436(4) |
| N(14) | H(141) | 0.85(4) | C(24) | C(25) | 1.394(4) |
| N(14) | H(142) | 0.76(4) | C(25) | C(26) | 1.351(5) |
| N(21) | C(26) | 1.337(4) | | | |

Numbers in parentheses are estimated standard deviations in the least significant digits.

FIG. 11

| Atom 1 | Atom 2 | Atom 3 | Angle | Atom 1 | Atom 2 | Atom 3 | Angle |
|---|---|---|---|---|---|---|---|
| O(3) | S(1) | O(4) | 113.82(19) | C(24) | N(24) | H(242) | 127(2) |
| O(3) | S(1) | O(1) | 109.71(17) | H(241) | N(24) | H(242) | 118(4) |
| O(4) | S(1) | O(1) | 109.31(15) | C(13) | C(12) | N(11) | 121.6(2) |
| O(3) | S(1) | O(2) | 108.94(19) | C(12) | C(13) | N(13) | 122.3(3) |
| O(4) | S(1) | O(2) | 107.95(17) | C(12) | C(13) | C(14) | 118.4(2) |
| O(1) | S(1) | O(2) | 106.86(13) | N(13) | C(13) | C(14) | 119.1(3) |
| H(1W1) | O(1W) | H(1W2) | 109(5) | N(14) | C(14) | C(15) | 121.3(3) |
| C(16) | N(11) | C(12) | 120.4(2) | N(14) | C(14) | C(13) | 120.8(3) |
| C(16) | N(11) | C(22) | 119.1(2) | C(15) | C(14) | C(13) | 117.8(2) |
| C(12) | N(11) | C(22) | 120.4(2) | C(16) | C(15) | C(14) | 121.0(3) |
| C(13) | N(13) | H(131) | 111(3) | C(15) | C(16) | N(11) | 120.6(3) |
| C(13) | N(13) | H(132) | 115(2) | N(21) | C(22) | C(23) | 123.1(3) |
| H(131) | N(13) | H(132) | 117(4) | N(21) | C(22) | N(11) | 116.1(2) |
| C(14) | N(14) | H(141) | 117(3) | C(23) | C(22) | N(11) | 120.8(2) |
| C(14) | N(14) | H(142) | 120(3) | N(23) | C(23) | C(22) | 122.4(3) |
| H(141) | N(14) | H(142) | 123(4) | N(23) | C(23) | C(24) | 120.9(3) |
| C(26) | N(21) | C(22) | 120.1(3) | C(22) | C(23) | C(24) | 116.6(3) |
| C(26) | N(21) | H(21) | 122(3) | N(24) | C(24) | C(25) | 122.3(3) |
| C(22) | N(21) | H(21) | 118(3) | N(24) | C(24) | C(23) | 119.6(3) |
| C(23) | N(23) | H(231) | 122(3) | C(25) | C(24) | C(23) | 118.0(3) |
| C(23) | N(23) | H(232) | 119(3) | C(26) | C(25) | C(24) | 121.4(3) |
| H(231) | N(23) | H(232) | 118(4) | N(21) | C(26) | C(25) | 120.7(3) |
| C(24) | N(24) | H(241) | 114(3) | | | | |

Numbers in parentheses are estimated standard deviations in the least significant digits.

FIG. 12

| D | H | A | D-H | A..H | D..A | D-H..A |
|---|---|---|---|---|---|---|
| O(31) | H(31) | O(4) | 0.819(3) | 1.939(3) | 2.753(5) | 172(2) |
| N(13) | H(131) | O(1) | 0.82(5) | 2.20(5) | 2.988(4) | 161(4) |
| N(13) | H(132) | S(1) | 1.16(5) | 2.70(5) | 3.682(3) | 141(3) |
| N(13) | H(132) | O(3) | 1.16(5) | 1.94(5) | 3.025(4) | 154(4) |
| N(14) | H(141) | S(1) | 0.85(4) | 2.97(4) | 3.804(3) | 167(3) |
| N(14) | H(141) | O(2) | 0.85(4) | 2.11(4) | 2.935(4) | 165(4) |
| N(14) | H(142) | O(1) | 0.76(4) | 2.19(5) | 2.909(4) | 158(4) |
| N(23) | H(231) | O(1W) | 0.93(5) | 2.04(5) | 2.959(5) | 171(4) |
| N(23) | H(232) | O(31) | 0.74(4) | 2.31(4) | 2.982(4) | 151(4) |
| N(24) | H(241) | O(3) | 0.86(4) | 1.97(4) | 2.767(4) | 155(4) |
| N(24) | H(242) | O(1W) | 0.95(4) | 1.91(4) | 2.856(4) | 174(3) |
| O(1W) | H(1W1) | S(1) | 0.87(7) | 2.76(8) | 3.622(3) | 170(6) |
| O(1W) | H(1W1) | O(2) | 0.87(7) | 2.20(7) | 3.024(4) | 158(6) |
| O(1W) | H(1W1) | O(4) | 0.87(7) | 2.28(7) | 2.991(4) | 139(6) |
| O(1W) | H(1W2) | S(1) | 0.78(5) | 2.87(5) | 3.641(3) | 173(5) |
| O(1W) | H(1W2) | O(1) | 0.78(5) | 2.02(6) | 2.759(4) | 158(5) |
| N(21) | H(21) | S(1) | 0.89(4) | 2.95(4) | 3.658(3) | 150(3) |
| N(21) | H(21) | O(2) | 0.80(4) | 1.94(4) | 2.736(4) | 176(4) |

Numbers in parentheses are estimated standard deviations in the least significant digits.

FIG. 13

| Atom 1 | Atom 2 | Atom 3 | Atom 4 | Angle |
|---|---|---|---|---|
| C(16) | N(11) | C(12) | C(13) | -2.07 ( 0.40) |
| C(22) | N(11) | C(12) | C(13) | 174.07 ( 0.25) |
| C(12) | N(11) | C(16) | C(15) | 2.16 ( 0.42) |
| C(22) | N(11) | C(16) | C(15) | -174.03 ( 0.27) |
| C(12) | N(11) | C(22) | N(21) | 71.59 ( 0.34) |
| C(12) | N(11) | C(22) | C(23) | -109.76 ( 0.32) |
| C(16) | N(11) | C(22) | N(21) | -112.22 ( 0.31) |
| C(16) | N(11) | C(22) | C(23) | 66.43 ( 0.36) |
| C(26) | N(21) | C(22) | N(11) | 177.18 ( 0.27) |
| C(26) | N(21) | C(22) | C(23) | -1.43 ( 0.47) |
| C(22) | N(21) | C(26) | C(25) | -0.46 ( 0.48) |
| N(11) | C(12) | C(13) | N(13) | -176.79 ( 0.27) |
| N(11) | C(12) | C(13) | C(14) | -1.35 ( 0.40) |
| N(13) | C(13) | C(14) | N(14) | -1.46 ( 0.45) |
| N(13) | C(13) | C(14) | C(15) | -179.87 ( 0.30) |
| C(12) | C(13) | C(14) | N(14) | -177.05 ( 0.29) |
| C(12) | C(13) | C(14) | C(15) | 4.54 ( 0.40) |
| N(14) | C(14) | C(15) | C(16) | 177.05 ( 0.31) |
| C(13) | C(14) | C(15) | C(16) | -4.56 ( 0.44) |
| C(14) | C(15) | C(16) | N(11) | 1.24 ( 0.45) |
| N(11) | C(22) | C(23) | N(23) | 2.36 ( 0.45) |
| N(11) | C(22) | C(23) | C(24) | -176.23 ( 0.25) |
| N(21) | C(22) | C(23) | N(23) | -179.09 ( 0.30) |
| N(21) | C(22) | C(23) | C(24) | 2.32 ( 0.44) |
| N(23) | C(23) | C(24) | N(24) | 1.08 ( 0.45) |
| N(23) | C(23) | C(24) | C(25) | 179.98 ( 0.39) |
| C(22) | C(23) | C(24) | N(24) | 179.69 ( 0.29) |
| C(22) | C(23) | C(24) | C(25) | -1.40 ( 0.41) |
| N(24) | C(24) | C(25) | C(26) | 178.54 ( 0.31) |
| C(23) | C(24) | C(25) | C(26) | -0.33 ( 0.46) |
| C(24) | C(25) | C(26) | N(21) | 1.31 ( 0.49) |

Numbers in parentheses are estimated standard deviations in the least significant digits.

FIG. 14

DETERMINING DEGRADATION OF 3,4-DIAMINOPYRIDINE

FIELD OF THE INVENTION

This disclosure relates to the field of pharmaceutical impurity detection and quantitation.

BACKGROUND OF THE INVENTION

Impurities, either synthetic or degradative, found in drug products or drug dosage forms have been associated with adverse effects including increased toxicity, decreased efficacy of the active drug, and other undesirable side effects. Such impurities, once identified, are reduced to the lowest possible levels to lessen the risk of adverse events. 3,4-Diaminopyridine is a central nervous system drug used in the treatment of Lambert/Eaton Myasthenic Syndrome (LEMS) and other rare muscle diseases. A great need exists for the ability to ascertain whether amounts of 3,4-diaminopyridine have degraded. It is greatly desired to be able to quantitate the amount of degradation present in a 3,4-diaminopyridine sample. There also exists a need for highly sensitive means of detecting impurities in a sample of 3,4-diaminopyridine, determining the purity of a sample of 3,4-diaminopyridine, and quantitating the amount of impurities present in a 3,4-diaminopyridine sample.

SUMMARY OF THE INVENTION

Disclosed herein are methods for ascertaining whether a quantity of 3,4-diaminopyridine has undergone significant degradation as well as ways for quantifying such degradation.

Methods for determining the purity of a sample of 3,4-diaminopyridine comprising determining the presence, absence, or amount of a dimer of 3,4-diaminopyridine in the form of a salt, solvate or complex or a combination thereof are also included in the present disclosure.

Methods are also provided for detecting and quantitating degradation in a sample of a of 3,4-diaminopyridine comprising subjecting the sample to high performance liquid chromatography to identify the presence or absence of a peak identified as a dimer of 3,4-diaminopyridine; subjecting a standard comprising a known amount of the dimer of 3,4-diaminopyridine or a derivative thereof to high performance liquid chromatography; and comparing the amount of the dimer of 3,4-diaminopyridine in the sample to the amount of the dimer of 3,4-diaminopyridine in the standard, each as identified by high performance liquid chromatography.

Compositions directed to 3,4-diaminopyridine dimer sulfate monohydrate monomethanolate are also disclosed.

Methods are also set forth for producing 3,4-diaminopyridine dimer sulfate monohydrate monomethanolate comprising dissolving 3,4-diaminopyridine; oxidizing the dissolved 3,4-diaminopyridine; and isolating 3,4-diaminopyridine dimer sulfate monohydrate monomethanolate.

BRIEF DESCRIPTION OF THE DRAWINGS

The summary, as well as the following detailed description, is further understood when read in conjunction with the appended drawings. For the purpose of illustrating the disclosed compositions and methods, there are shown in the drawings exemplary embodiments of the compositions and methods; however, the compositions and methods are not limited to the specific embodiments disclosed. In the drawings:

FIG. 3 summarizes crystal data and crystallographic data collection parameters,

FIG. 9 illustrates the positional parameters and their estimated standard deviations of 3,4-diaminopyridine dimer sulfate monohydrate monomethanolate.

FIG. 10 illustrates the anisotropic displacement factor coefficients of 3,4-diaminopyridine dimer sulfate monohydrate monomethanolate.

FIG. 11 illustrates the bond distances of 3,4-diaminopyridine dimer sulfate monohydrate monomethanolate.

FIG. 12 illustrates the bond angles of 3,4-diaminopyridine dimer sulfate monohydrate monomethanolate.

FIG. 13 illustrates the hydrogen bonds and angles of 3,4-diaminopyridine dimer sulfate monohydrate monomethanolate.

FIG. 14 illustrates the torsion angles of 3,4-diaminopyridine dimer sulfate monohydrate monomethanolate.

DETAILED DESCRIPTION OF ILLUSTRATIVE EMBODIMENTS

Figure 1:
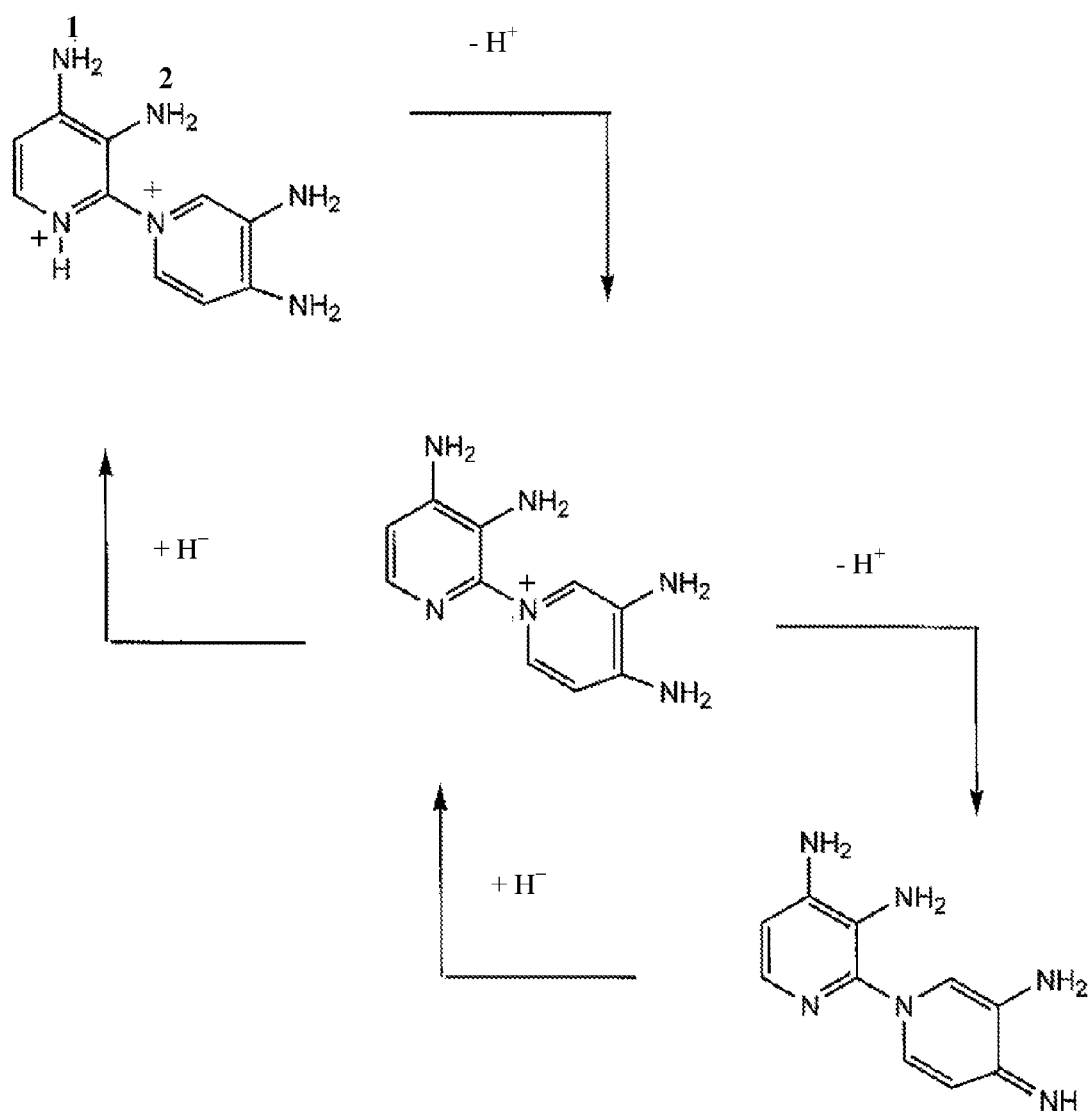
FIG. 1 illustrates structural variations of a dimer of 3,4-diaminopyridine.

The disclosed compositions and methods may be understood more readily by reference to the following detailed description taken in connection with the accompanying figures, which form a part of this disclosure. It is to be understood that the disclosed compositions and methods are not limited to the specific compositions and methods described and/or shown herein, and that the terminology used herein is for the purpose of describing particular embodiments by way of example only and is not intended to be limiting of the claimed compositions and methods.

Unless specifically stated otherwise, any description as to a possible mechanism or mode of action or reason for improvement is meant to be illustrative only, and the disclosed compositions and methods are not to be constrained by the correctness or incorrectness of any such suggested mechanism or mode of action or reason for improvement.

Throughout this text, the descriptions refer to compositions and methods of using said compositions. Where the disclosure describes or claims a feature or embodiment associated with a composition, such a feature or embodiment is equally applicable to the methods of using said composition. Likewise, where the disclosure describes or claims a feature or embodiment associated with a method of using a composition, such a feature or embodiment is equally applicable to the composition.

When a range of values is expressed, another embodiment includes from the one particular value and/or to the other particular value. Further, reference to values stated in ranges include each and every value within that range. All ranges are inclusive and combinable. When values are expressed as approximations, by use of the antecedent "about," it will be understood that the particular value forms another embodiment. Reference to a particular numerical value includes at least that particular value, unless the context clearly dictates otherwise.

The term "about" when used in reference to numerical ranges, cutoffs, or specific values is used to indicate that the recited values may vary by up to as much as 10% from the listed value. As many of the numerical values used herein are experimentally determined, it should be understood by those skilled in the art that such determinations can, and often times will, vary among different experiments. The values used herein should not be considered unduly limiting by virtue of this inherent variation. Thus, the term "about" is used to encompass variations of ±10% or less, variations of ±5% or less, variations of ±1% or less, variations of ±0.5% or less, or variations of ±0.1% or less from the specified value.

It is to be appreciated that certain features of the disclosed compositions and methods which are, for clarity, described herein in the context of separate embodiments, may also be provided in combination in a single embodiment. Conversely, various features of the disclosed compositions and methods that are, for brevity, described in the context of a single embodiment, may also be provided separately or in any subcombination.

As used herein, the singular forms "a," "an," and "the" include the plural.

Various terms relating to aspects of the description are used throughout the specification and claims. Such terms are to be given their ordinary meaning in the art unless otherwise indicated. Other specifically defined terms are to be construed in a manner consistent with the definitions provided herein.

Pharmaceutical compositions degrade over time and the resulting degradation products can signify that the active ingredient is no longer capable of eliciting the desired therapeutic effect. In some instances, degradation products can cause adverse events for those taking the medication. Therefore, assessing dosage forms of a pharmaceutical for the presence of impurities and degradation products is necessary for proper quality control.

This invention relates generally to the identification of a degradation product of 3,4-diaminopyridine. This invention also relates to methods of synthesizing the degradation product of 3,4-diaminopyridine, as well as methods of analyzing a sample of 3,4-diaminopyridine for the presence of a degradation product. The invention also relates to using a synthesized degradation product as a reference marker for use in detecting and quantifying the amount of a degradation product in a sample of 3,4-diaminopyridine, or a pharmaceutically acceptable salt thereof.

We have determined that degradation of 3,4-diaminopyridine can be evidenced by the presence of a dimer of 3,4-diaminopyridine or a dimer having certain salt, solvate or alcoholate derivatives. Ascertaining the presence or absence of such dimers in samples of 3,4-diaminopyridine indicates the presence or absence of degradation.

We have identified 3,4-diaminopyridine dimer sulfate monohydrate monomethanolate as a novel compound that can be used to assess the presence of degradation in a sample of 3,4-diaminopyridine. Although two 3,4-diaminopyridine molecules are covalently linked to form the 3,4-diaminopyridine dimer, the dimer is not symmetrical. For example, in some embodiments the dimer has the following structure, and tautomers thereof:

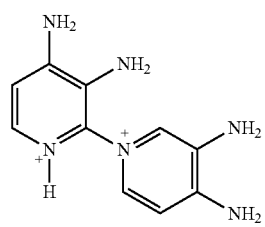

In alternative embodiments the dimer has the following structure, and tautomers thereof:

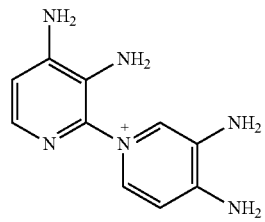

In other embodiments, the dimer has the following structure:

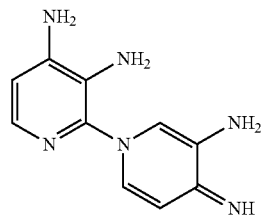 [SMILES: N=c1ccn(-c2nccc(N)c2N)cc1N]

The structures represented above illustrate different pH-dependent forms of dimers of 3,4-diaminopyridine. FIG. 1 further depicts the effect of pH on the dimer by illustrating different charge configurations in changing pH environments. In environments where counterions are present, the above shown compounds can form quaternary salts. For example, sulfate counterions produce a sulfate quaternary salt of the dimer. Thus, it is possible to expose the dimer present in a sample of 3,4-diaminopyridine to an environment that yields a readily identifiable form of the dimer, which can serve as an indicator of degradation of 3,4-diaminopyridine. In some embodiments, the sample can be a pharmaceutical dosage form of 3,4 diaminopyridine.

Some embodiments of the invention provide a 3,4-diaminopyridine dimer in the form of a salt, solvate, or complex or a combination thereof. In some embodiments of the invention, the salt comprises a sulfate. Those skilled in the art will recognize that the counterion for these quaternary salts are not limited to sulfate salts, and other salt forms of the dimer can be identified through routine experimentation. In some embodiments of the present invention, the dimer is in the form of a solvate. In some aspects, the solvate comprises a monomethanolate. Those skilled in the art will recognize that the solvate form of the dimer can comprise other compounds than monomethanolate and other solvate forms of the dimer can be identified with routine experimentation. For example, the solvate form can comprise other alcoholates.

The dimer, in some embodiments, is in the form of a complex. In some embodiments, the complex comprises a monohydrate. In some aspects, the complex involves a compound or molecule capable of binding or otherwise interacting with the dimer. The molecule in some embodiments is water. Those skilled in the art will know that other compounds and molecules can be identified through routine experimentation that complex with the dimer. In some embodiments, the 3,4-diaminopyridine dimer is in the form of a salt, a solvate, and complex. In some aspects, the 3,4-diaminopyridine dimer comprises at least one sulfate, at least one monohydrate, and at least one monomethanolate. In some embodiments the 3,4-diaminopyridine dimer is 3,4-diaminopyridine dimer sulfate monohydrate monomethanolate. In some aspects the solvent, salt, and complex ratio is about 1:1:1, while in other embodiments the ratio is about 1:1:1.5. Those skilled in the art will recognize that other ratios are possible and can be produced with routine experimentation.

Figure 2:
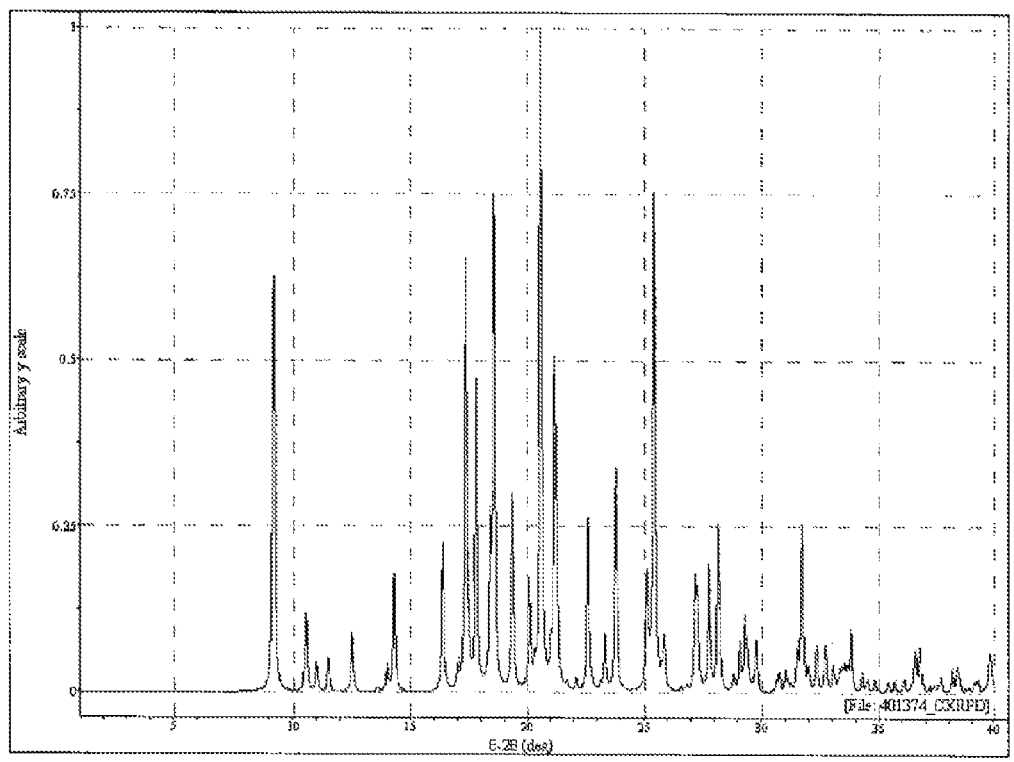
FIG. 2 illustrates the calculated X-ray powder pattern of 3,4-diaminopyridine dimer sulfate monohydrate monomethanolate.

In some aspects of the present invention, 3,4-diaminopyridine dimer sulfate monohydrate monomethanolate is an amorphous solid. While the 3,4-diaminopyridine dimer can be amorphous, crystalline forms, such as a sulfate salt crystalline form of a 3,4-diaminopyridine dimer, can also be produced. The X-Ray powder pattern of 3,4-diaminopyridine dimer sulfate monohydrate monomethanolate as shown in FIG. 2 depicts a crystal form of the dimer.

A 3,4-diaminopyridine dimer can be in the form of an oil. For example, a crude dimer can be produced by oxidizing a dissolved sample of 3,4-diaminopyridine. The crude dimer can be distilled from the oxidation reaction by first mixing the oxidation reaction with activated, basic aluminum oxide. After water is removed under reduced pressure, the residue is loaded onto an aluminum oxide column and eluted with acetonitrile/water. The resulting dimer will be in an oil form.

Alternatively, the oil form of the crude dimer can be produced by mixing the oxidation reaction with silica gel. After removing water under pressure, the residue is loaded onto a silica gel column and eluted first with methanol/triethylamine and then methanol. A further elution with methanol/formic acid results in a crude dimer oil.

In another aspect of the present invention, a method is provided of determining the purity of a sample of 3,4-diaminopyridine comprising determining the presence, absence, or amount of a dimer of 3,4-diaminopyridine in the form of a salt, solvate or complex or a combination thereof. In some embodiments, 3,4-diaminopyridine dimer sulfate monohydrate monomethanolate is the dimer of 3,4-diaminopyridine.

Synthesized 3,4-diaminopyridine dimer sulfate monohydrate monomethanolate is suitable for use as a reference marker in a quantitative analysis when determining the amount dimer present in a sample. In some embodiments, determining the amount of the dimer of 3,4-diaminopyridine comprises fractionating the sample by high performance liquid chromatography (HPLC). HPLC, also referred to as high pressure liquid chromatography, can be used to fractionate a sample and detect the distinct fractions. HPLC analysis typically comprises injecting a sample onto a column and then eluting distinct fractions containing the sample components over time. The eluted fractions are detected, usually by ultraviolet absorption, and a chromatogram is generated to graphically represent the relative elution times. Compounds present in the sample being analyzed with HPLC can have different retention times, thus allowing identification of an active pharmaceutical ingredient (API), degradation products of the API, or other impurities present in the dosage or bulk form of the drug. The area under the retention peaks of the chromatogram can be measured to determine a concentration or amount of a compound present in a sample.

In one aspect of the present invention, when fractionating a degraded sample of 3,4-diaminopyridine using HPLC, the known retention time of the reference sample allows for quantifying the amount of the dimer of 3,4-diaminopyridine and relating the same to the amount of 3,4-diaminopyridine in the sample. Comparing the area under the HPLC peak for the known amount of the reference sample of the dimer to the area under the HPLC peak for the dimer present in a sample of 3,4-diaminopyridine allows a determination regarding the purity of the sample. Ascertaining whether the amount of dimer of 3,4-diaminopyridine is greater than a predetermined mole percentage of dimer of 3,4-diaminopyridine in the sample provides a standardized metric to assess sample purity. In some aspects, the methods of the present invention can be employed to determine if the purity of a sample has degraded to an extent such that the sample will not be suitable for therapeutic uses. In other aspects, the methods can be used to monitor a bulk supply of 3,4-diaminopyridine or to gauge remaining shelf life.

In some aspects of the present invention, the predetermined mole percentage of the degradation product is between about 0.1 and about 1 mole percent. In some aspects the predetermined mole percentage is between about 0.1 and about 0.9 mole percent. In some aspects of the present invention, the predetermined mole percentage is between about 0.1 and about 0.8 mole percent. In some aspects of the present invention, the predetermined mole percentage is between about 0.1 and about 0.7 mole percent. In some aspects of the present invention, the predetermined mole percentage is between about 0.1 and about 0.6 mole percent. In some aspects of the present invention, the predetermined mole percentage is between about 0.1 and about 0.5 mole percent. In some aspects of the present invention, the predetermined mole percentage is between about 0.1 and about 0.4 mole percent. In some aspects of the present invention, the predetermined mole percentage is between about 0.1 and about 0.3 mole percent. In still other aspects of the present invention, the predetermined mole percent is about 0.1 and about 0.2 mole percent. In some aspects, the predetermined mole percent is less than 0.1 mole percent. In some aspects, the predetermined mole percent is less than 0.1 mole percent.

In other aspects of the present invention, the predetermined mole percentage is between about 0.2 and about 1 mole percent. In some aspects of the present invention, the predetermined mole percentage is between about 0.3 and about 1 mole percent. In some aspects of the present invention, the predetermined mole percentage is between about 0.4 and about 1 mole percent. In some aspects of the present invention, the predetermined mole percentage is between about 0.5 and about 1 mole percent. In some aspects of the present invention, the predetermined mole percentage is between about 0.6 and about 1 mole percent. In some aspects of the present invention, the predetermined mole percentage is between about 0.7 and about 1 mole percent. In some aspects of the present invention, the predetermined mole percentage is between about 0.8 and about 1 mole percent. In some aspects of the present invention, the predetermined mole percentage is between about 0.9 and about 1 mole percent. In some embodiments of the present invention, said predetermined mole percentage is about 0.5 mole percent, about 0.4 mole percent, about 0.3 mole percent, about 0.2 mole percent, and even about 0.1 mole percent.

Another aspect of the present invention provides a method of detecting and quantitating degradation in a sample of 3,4-diaminopyridine comprising subjecting the sample to high performance liquid chromatography to identify the presence or absence of a peak identified as a dimer of 3,4-diaminopyridine; subjecting a standard comprising a known amount of the dimer to high performance liquid chromatography; and comparing the amount of the dimer of 3,4-diaminopyridine in the sample to the amount of the dimer of 3,4-diaminopyridine in the standard, each as identified by high performance liquid chromatography. In some embodiments, the sample comprises a pharmaceutical dosage form. A "pharmaceutical dosage form" refers to the form of the compound ingested or otherwise received by a patient. Common oral pharmaceutical dosage forms include, but are not limited to, powders, pills, and liquids. Pharmaceutical dosage forms can be a mixture of the active ingredient with excipients, or nondrug components.

In some aspects of the method, the dimer of 3,4-diaminopyridine is a degradation product of 3,4-diaminopyridine. In some aspects, the dimer of 3,4-diaminopyridine is in the form of a salt, solvate, or complex or a combination thereof. In some embodiments, the dimer of 3,4-diaminopyridine is 3,4-diaminopyridine sulfate monohydrate monomethanolate.

Some embodiments of the present invention provide that the standard comprising a known amount of 3,4-diaminopyridine differs in molecular weight from the 3,4-diaminopyridine present in the sample. In some embodiments, the 3,4-diaminopyridine standard comprises an isotopic substitution, and in some aspects the isotopic substitution is deuterium, carbon-13, or nitrogen-15. In other embodiments, the 3,4-diaminopyridine standard comprises a radiolabel.

Degradation of a sample can depend on a variety of conditions including time, storage conditions, and exposure to other environmental conditions. Improper storage temperature and/or humidity, for example, can increase the rate of degradation of an active pharmaceutical ingredient. Furthermore, processing a stored or bulk form of a drug into a pharmaceutical dose form can result in a different degradation rate for the active ingredient. It is therefore important to determine the rates of degradation of a sample at multiple time points during the manufacturing process as well as during storage of both bulk and pharmaceutical composition of the drug to ensure a patient is receiving an adequate amount of active ingredient and not more than an acceptable level of degradation product. Thus, the present invention provides for more than one subsample being analyzed over time to determine a rate of degradation of the sample. In one aspect of the invention, more than one sample of the dosage form is analyzed over time to determine a rate of degradation of the dosage form.

Another aspect of the present invention provides a method of producing 3,4-diaminopyridine dimer sulfate monohydrate monomethanolate comprising dissolving 3,4-diaminopyridine in a solvent; oxidizing the dissolved 3,4-diaminopyridine; and isolating the 3,4-diaminopyridine dimer sulfate monohydrate monomethanolate. A suitable solvent for dissolving 3,4-diaminopyridine is methanol or methanol and water, however other solvents may be employed and suitable solvents can be readily identified by one skilled in the art. Once dissolved, an appropriate oxidant can oxidize the dissolved 3,4-diaminopyridine to generate the desired 3,4-diaminopyridine dimer. In some embodiments, hydrogen peroxide oxidizes the dissolved 3,4-diaminopyridine although other oxidants can be employed. Again, a skilled person can determine oxidants suitable for use in producing the dimer through routine experimentation.

Another embodiment of the invention provides a method of isolating 3,4-diaminopyridine dimer sulfate monohydrate monomethanolate comprising slurrying the 3,4-diaminopyridine dimer solution with aluminum oxide; evaporating water from the slurry to form a dried material; separating a dimer from the dried material using a separation technique; dissolving the separated dimer in methanol and water; treating the dissolved dimer with a methanolic solution of concentrated sulfuric acid to form a product mixture; adding ethyl acetate to the product mixture; and isolating the dimer sulfate salt solvate complex. Separating a dimer can be accomplished, for example, by fractionating the oxidation reaction by column chromatography.

EXAMPLES

The following examples are provided to further describe some of the embodiments disclosed herein. The examples are intended to illustrate, not to limit, the disclosed embodiments.

Example 1

Synthesis of 3,4-Diaminopyridine Dimer Sulfate Monohydrate Monomethanolate.

33 g of 3,4-diaminopyridine was dissolved in 700 mL of water to form a slurry. 69.0 g of 30% hydrogen peroxide was added to the slurry to oxidize the 3,4-diaminopyridine. The reaction was carried out at room temperature and monitored by thin layer chromatography. After one month, the reaction produced the highest concentration of 3,4-diaminopyridine dimer. 25 mL of the oxidation reaction mixture was then mixed with 25 g of activated, basic aluminum oxide. The mixture was distilled under reduced pressure to remove water. The resulting residue was loaded onto an aluminum oxide column. Fractions were eluted from the column using methanol/water (from 100:0 to 5:1). Desired fractions were distilled under reduced pressure to yield 56 mg of dimer as a brown oil.

The dimer was dissolved in a mixture of water and methanol. 4.0 equivalents of concentrated sulfuric acid in methanol were added to the dissolved dimer. Ethyl acetate was then added, and the solution was filtered through a syringe filter. The solution was incubated at room temperature overnight. The supernatant was decanted to yield less than 15 mg of the desired 3,4-diaminopyrimidine dimer sulfate monohydrate monomethanolate.

Example 2

Synthesis of 3,4-Diaminopyridine Dimer Sulfate 1.5 Monohydrate Monomethanolate.

150 mL of the oxidation reaction of Example 1 was mixed with 50 g of silica gel. The mixture was distilled under reduced pressure to remove water. The residue was then loaded onto a silica gel column. Fractions were eluted from the column with methanol/triethylamine (20:1, 1000 mL), then methanol (900 mL). Further elution was carried out with methanol/formic acid (100:1, 900 mL), and the desired fractions were distilled under reduced pressure to yield 3.323 g of a brown hazy oil. 2.9 g of the oil was dissolved in a mixture of 2.5 mL of methanol and 1.5 mL of water. This dimer solution was then added dropwise to a sulfuric acid solution, which was prepared by adding 1.447 g of 98% sulfuric acid (1.1 equivalents) into 15 mL of methanol. The resulting slurry was stirred for 10 minutes, then filtered. The filtrate was rinsed with methanol and suction dried to yield 1.211 g of 3,4-diaminopyridine dimer sulfate 1.5 monohydrate monomethanolate in a tan solid form.

Example 3

Isocratic Reversed Phase HPLC Detection and Quantitation of 3,4-Diaminopyridine Dimer Sulfate Monohydrate Monomethanolate A stock reference standard was prepared by dissolving 43 mg of 3,4-diaminopyridine dimer sulfate monohydrate monomethanolate in 50 mL of final mobile phase. A 3,4-diaminopyridine stock reference standard was prepared by dissolving 25 mg of 3,4-diaminopyridine in 50 mL of final mobile phase. The final concentrations of both standards were 250 µg/mL. Resolution standards were prepared by diluting the stock reference standards to a final concentration of 5 µg/mL. Working standards were prepared by diluting the stock reference standards to a final concentration of 1 µg/mL.

Samples to be analyzed were prepared by randomly selecting and weighing 20 3,4-diaminopyridine tablets. The tablets were ground to a fine powder and about 50 mg of the powder was dissolved in 50 mL of final mobile phase. The sample was sonicated for two minutes with occasional shaking. The sonicated sample was then mechanically shaken for an additional 30 minutes and filtered using a 0.45 µm Microsolve filter.

Analytical separations were performed using 20 µL samples injected onto a C18 column, a 1.0 mL/min flow rate, detection at 254 nm, and a total run time of 60 minutes. Mobile phase A was prepared by dissolving about 1 g of octane sulfonic acid sodium salt and 2.31 g of ammonium acetate in 1000 mL of purified water. pH was adjusted to 4.0 (±0.05) with trifluoroacetic acid. Mobile Phase B consisted of HPLC grade acetonitrile. The final mobile phase was prepared by mixing 900 mL of Mobile Phase A and 100 mL of Mobile Phase B, the mixture being degassed. The retention time for 3,4-diaminopyridine was 14.5 minutes and 39.0 minutes for 3,4-diaminopyridine dimer sulfate monohydrate monomethanolate.

Example 4

Crystal Structure of 3,4-Diaminopyridine Dimer Sulfate Monohydrate Monomethanolate The structure of a sample of 3,4-diaminopyridine dimer was determined by single crystal X-ray diffraction.

The orthorhombic cell parameters and calculated volume are: a=10.4259(4) Å, b=16.7836(9) Å, c=19.2638(7) Å ($\alpha=\beta=\gamma=90°$), V=3370.9(3) Å$^3$. The formula weight of the asymmetric unit in the crystal structure of 3,4-diaminopyridine dimer sulfate monohydrate monomethanolate is 364.39 g/mol with Z=8, resulting in a calculated density of 1.436 g/cm$^3$. The space group was determined to be Pbca (no. 61). A summary of the crystal data and crystallographic data collection parameters are provided in FIG. 3.

The quality of the structure obtained is high, as indicated by the fit residual, R of 0.0565 (5.65%). R-values in the range of 0.02 to 0.06 are quoted for the most reliably determined structures (Glusker et al., Crystal *Structure Analysis: A Primer*, 2d ed., Oxford Univ. Press, New York (1985), p. 87).

Figure 4:
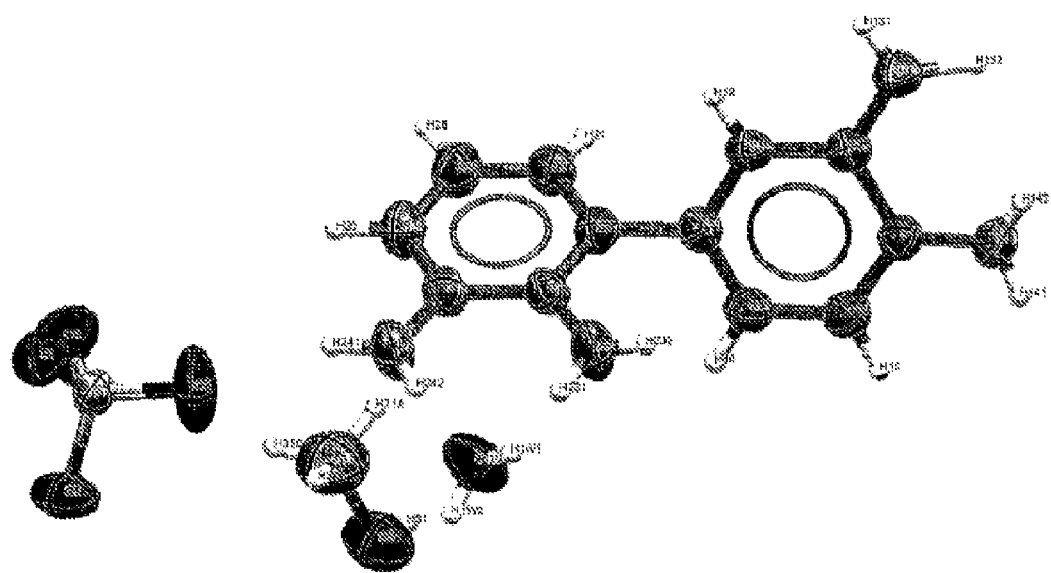
FIG. 4 illustrates the atomic displacement ellipsoid of 3,4-diaminopyridine dimer sulfate monohydrate monomethanolate.

An atomic displacement ellipsoid drawing of 3,4-diaminopyridine dimer sulfate monohydrate monomethanolate is shown in FIG. 4. The molecule observed in the asymmetric unit of the single crystal structure is consistent with a dimer unit of 3,4-diaminopyridine. The asymmetric unit shown in FIG. 4 contains one 3,4-diaminopyridine dimer cation, one sulfate anion, one water molecule, and one methanol molecule. One hydrogen was located and refined independently on the pyridine nitrogen. The other positive charge shown in FIG. 4 is on the bridging pyridine nitrogen. However, the charge is delocalized over the diaminopyridine moiety.

Figure 5:
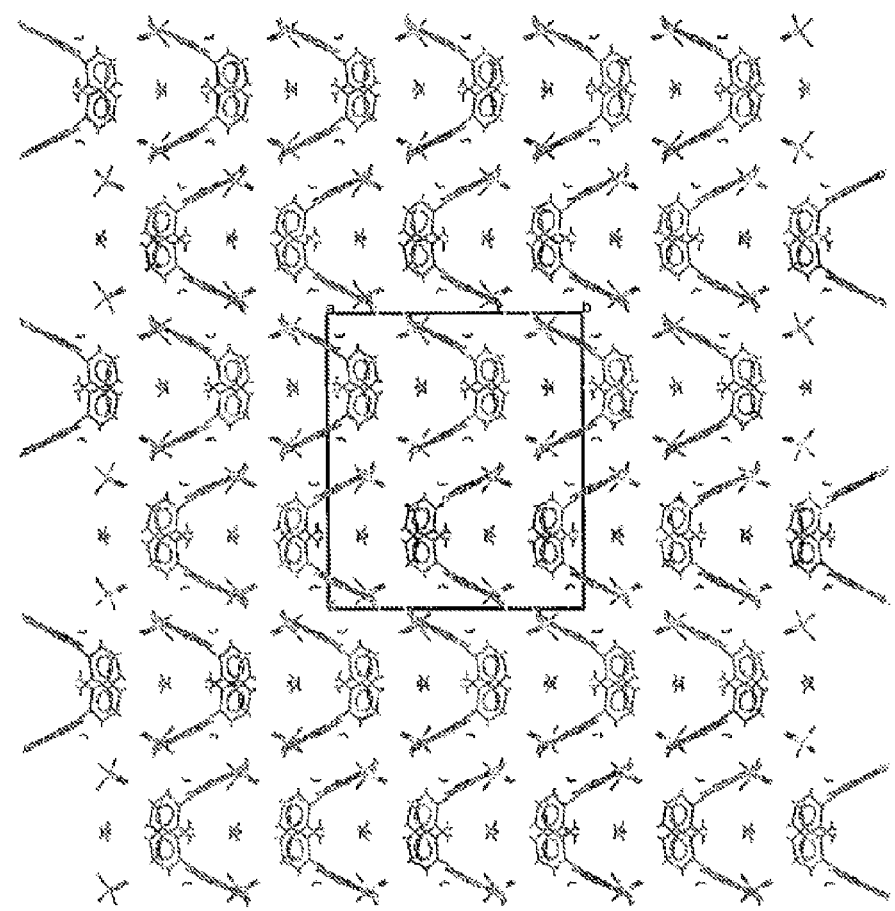
FIG. 5 is a packing diagram of 3,4-diaminopyridine dimer sulfate monohydrate monomethanolate viewed along the a crystallographic axis.
Figure 6:
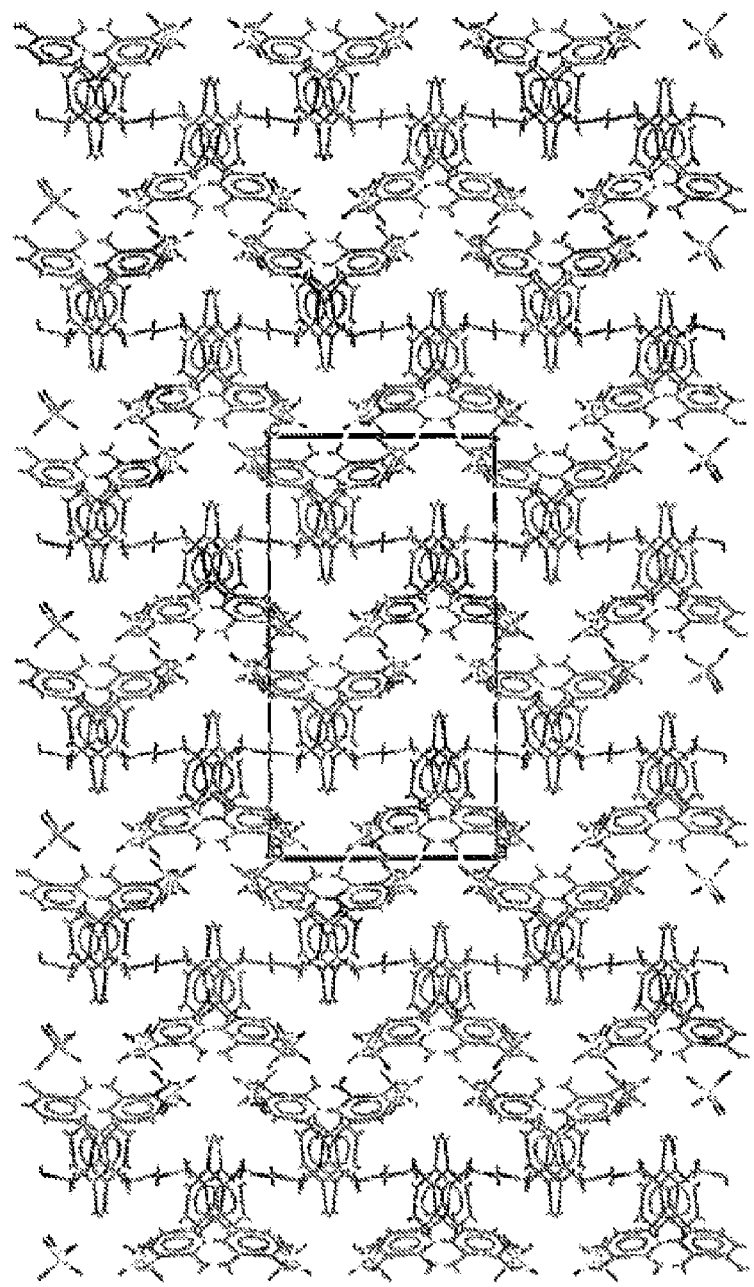
FIG. 6 is a packing diagram of 3,4-diaminopyridine dimer sulfate monohydrate monomethanolate viewed along the b crystallographic axis.
Figure 7:
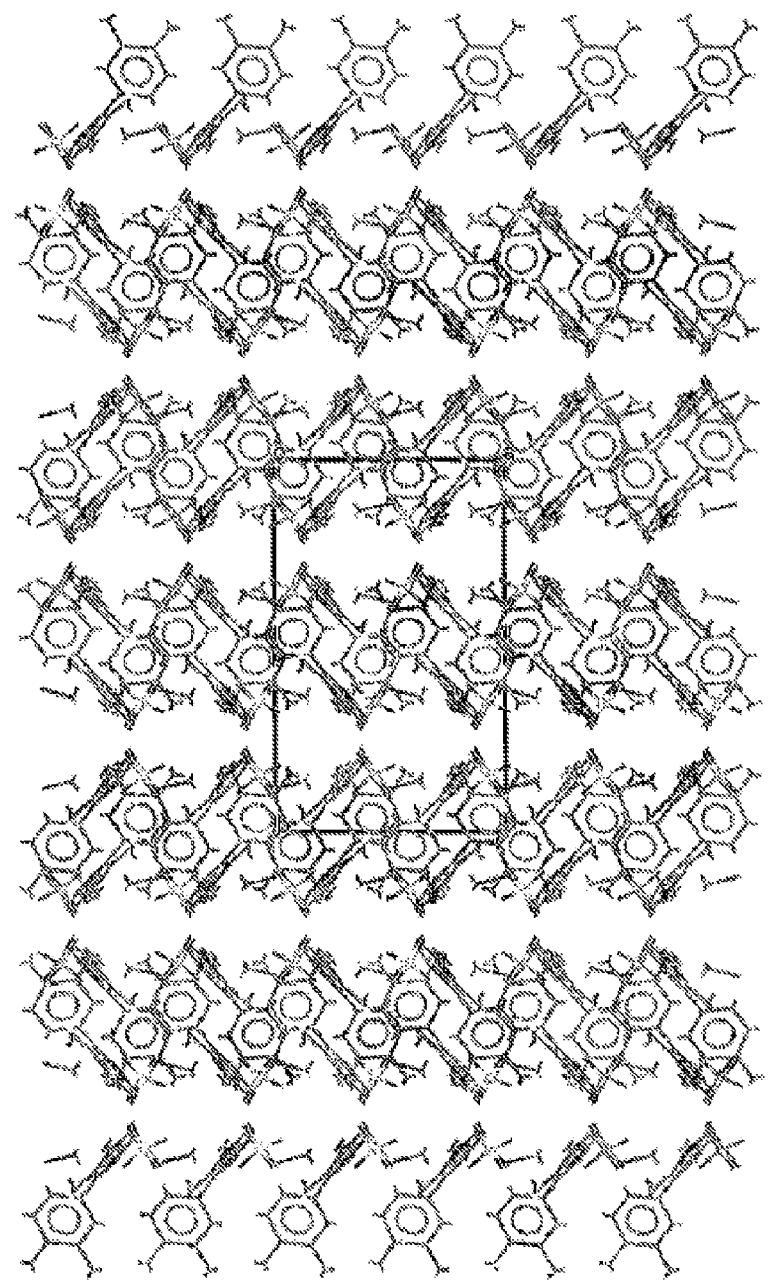
FIG. 7 is a packing diagram of 3,4-diaminopyridine dimer sulfate monohydrate monomethanolate viewed along the c crystallographic axis.
Figure 8:
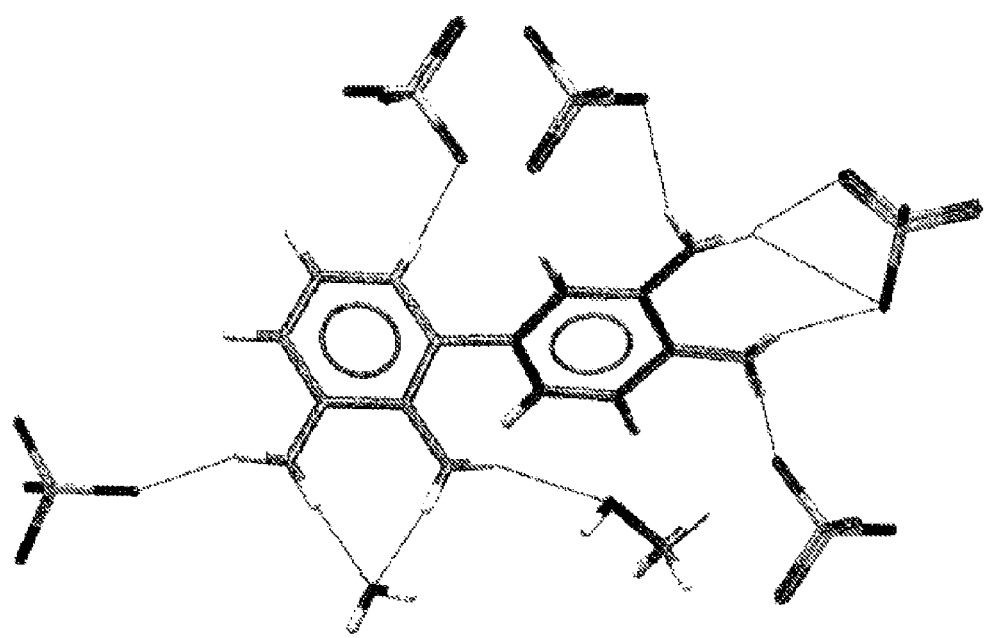
FIG. 8 illustrates the hydrogen bonding environment surrounding the 3,4-diaminopyridine dimer.

Packing diagrams viewed along the a, b, and c crystallographic axes are shown in FIGS. 5-7, respectively. The hydrogen bonding environment surrounding the 3,4-diaminopyridine dimer is shown in FIG. 8, and results in a complex three dimensional hydrogen bond network.

FIG. 2 shows a calculated XRPD pattern of 3,4-diaminopyridine dimer sulfate monohydrate monomethanolate, generated from the single crystal structure.

FIGS. 9-14 depict positional parameters and their estimated standard deviations, anisotropic displacement factor coefficients, bond distances, bond angles, hydrogen bonds and angles, and torsion angles of 3,4-diaminopyridine dimer sulfate monohydrate monomethanolate, respectively.

A yellow plate of $C_{11}H_2ON_6O_6S$ [$O_4S$, $H_2O$, $CH_4O$, $C_{10}H_{14}N_6$] having approximate dimensions of 0.25×0.15× 0.08 mm, was mounted on a nylon loop in random orientation. Preliminary examination and data collection were performed with Cu Kα radiation ($\lambda=1.54178$ Å) on a Rigaku Rapid II diffractometer equipped with confocal optics. Refinements were performed using SHELX2013 (Sheldrick, G. M. *Acta Cryst.*, 2008, A64, 112).

Cell constants and an orientation matrix for data collection were obtained from least-squares refinement using the setting angles of 13873 reflections in the range $4°<\theta<67°$. The refined mosaicity form DENZO/SCALEPACK (Otwinowski, Z.; Minor, W. *Methods Enzymol.* 1997, 276, 307) was 0.31° indicating good crystal quality. The space group was determined by the program XPREP. From the systematic presence of the following conditions: 0k1 k=2n; h01 1=2n; hk0 h=2n, and from subsequent least-squares refinement, the space group was determined to be Pbca (no. 61). The data collected to a maximum diffraction angle (2θ) of 133.16° at room temperature.

Frames were integrated with HKL3000 (Otwinowski, Z.; Minor, W. *Methods Enzymol.* 1997, 276, 307). A total of 13873 reflections were collected, of which 2838 were unique. Lorentz and polarization corrections were applied to the data. The linear absorption coefficient is 2.097 mm$^{-1}$ for Cu Kα radiation. An empirical absorption correction using SCALEPACK was applied. Transmission coefficients ranged from 0.057 to 0.846. A secondary extinction correction was applied (Glusker et al., *Crystal Structure Analysis: A Primer*, 2nd ed.; Oxford University press: New York, 1985; p. 87). The final coefficient, refined in least squares, was 0.0020(3) (in absolute units). Intensities of equivalent reflections were averaged. The agreement factor for the averaging was 4.3% based on intensity.

Structure Solution and Refinement

The structure was solved by direct methods using SHELXT (Sheldrick, G. M. *Acta Cryst.*, 2008, A64, 112). The remaining atoms were located in succeeding difference Fourier syntheses. Hydrogen atoms that reside on nitrogen and oxygen were refined independently. All other hydrogen atoms were included in the refinement but restrained to ride on the atom to which they are bonded. The structure was refined in full matrix least-squares by minimizing the function:

$$\Sigma_w(|F_o|^2-|F_c|^2)^2$$

The weight w is defined as $1/[\sigma^2(F_0^2)+(0.0984P)^2+(2.0030P)]$, where $P=(F_o^2+2F_c^2)/3$.

Scattering factors were taken from the "International Tables for Crystallography," (International Tables for Crystallography, Vol. C, Kluwer Academic Publishers: Dordrecht, The Netherlands, 1992, Tables 4.2.6.8 and 6.1.1.4). Of the 2838 reflections used in the refinements, only the reflections with $F_o^2 > 2\sigma(F_o^2)$ were used in calculating the fit residual, R. A total of 2355 reflections were used in the calculation. The final cycle of refinement included 264 variable parameters and converged (largest parameter shift was <0.01 times its estimated standard deviation) with unweighted and weighted agreement factors of:

$$R=\Sigma|F_o-F_c|/\Sigma F_o=0.0565$$

$$R_w=(\Sigma w(F_o^2-F_c^2)^2/\Sigma w(F_o^2)^2)^{1/2}=0.1596$$

The standard deviation of an observation of unit weight (goodness of fit) was 1.053. The highest peak in the final difference Fourier had a height of 0.574 e/Å$^3$. The minimum negative peak had a height of −0.282 e/Å$^3$.

Calculated X-Ray Powder Diffraction (XRPD) Pattern

FIG. 2 depicts a calculated XRPD pattern generated for Cu radiation using Mercury (Macrae, C. F. et al., J. Appl. Cryst., 2006, 39, 453-457), and the atomic coordinates, space group, and unit cell parameters from the single crystal structure.

Atomic Displacement Ellipsoid and Packing Diagrams

The atomic displacement ellipsoid diagram was prepared using Mercury. Atoms are represented by 50% probability anisotropic thermal ellipsoids. Packing diagrams and additional figures were also generated with Mercury. Hydrogen bonding is represented as dashed lines.

CONCLUSION

The single crystal structure of a 3,4-diaminopyridine dimer was determined to be a hydrated and methanol solvated sulfate salt of a 3,4-diaminopyridine dimer. The crystal structure is composed of one dimer cation, one sulfate anion, one water molecule, and one methanol molecule in the asymmetric unit.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A method of detecting and quantitating degradation in a sample of 3,4-diaminopyridine comprising:
   subjecting the sample to high performance liquid chromatography to identify the presence or absence of a peak identified as a dimer of 3,4-diaminopyridine;
   subjecting a standard comprising a known amount of the dimer of 3,4-diaminopyridine or a derivative thereof to high performance liquid chromatography; and
   comparing the amount of the dimer of 3,4-diaminopyridine in the sample to the amount of the dimer of 3,4-diaminopyridine in the standard, each as identified by high performance liquid chromatography.

2. The method of claim 1, wherein the dimer of 3,4-diaminopyridine is a degradation product of 3,4-diaminopyridine.

3. The method of claim 1, wherein the dimer of 3,4-diaminopyridine in the form of a salt, solvate, or complex, or a combination thereof.

4. The method of claim 1, wherein more than one subsample is analyzed over time to determine a rate of degradation of the sample.

5. The method of claim 1, wherein the 3,4-diaminopyridine dimer standard differs from the 3.4-diaminopyrimidine dimer in molecular weight.

6. The method of claim 1, wherein the 3,4-diaminopyridine dimer standard comprises a radiolabel.

7. The method of claim 1, wherein the 3,4-diaminopyridine dimer standard comprises an isotopic substitution.

8. The method of claim 7, wherein the isotopic substitution is deuterium, carbon 13, carbon 14, nitrogen 15, oxygen 17, or oxygen 18.

* * * * *